United States Patent
Weber

(10) Patent No.: US 10,624,654 B2
(45) Date of Patent: Apr. 21, 2020

(54) PATIENT-SPECIFIC TRIAL REPOSITIONING BLOCK

(76) Inventor: Christoph Weber, Sins (CH)

( * ) Notice: Subject to any disclaimer, the term of this patent is extended or adjusted under 35 U.S.C. 154(b) by 1441 days.

(21) Appl. No.: 14/000,601

(22) PCT Filed: Feb. 17, 2012

(86) PCT No.: PCT/EP2012/052814
§ 371 (c)(1),
(2), (4) Date: Oct. 31, 2013

(87) PCT Pub. No.: WO2012/113735
PCT Pub. Date: Aug. 30, 2012

(65) Prior Publication Data
US 2014/0052136 A1 Feb. 20, 2014

(30) Foreign Application Priority Data
Feb. 21, 2011 (CH) .................................. 301/11

(51) Int. Cl.
| *A61B 17/16* | (2006.01) |
| *A61F 2/46* | (2006.01) |
| *A61B 17/15* | (2006.01) |
| *B33Y 70/00* | (2020.01) |
| *B33Y 80/00* | (2015.01) |
| *A61F 2/38* | (2006.01) |
| *A61B 17/56* | (2006.01) |

(52) U.S. Cl.
CPC ........ *A61B 17/1675* (2013.01); *A61B 17/155* (2013.01); *A61F 2/4684* (2013.01); *A61B 2017/568* (2013.01); *A61F 2/38* (2013.01); *B33Y 70/00* (2014.12); *B33Y 80/00* (2014.12)

(58) Field of Classification Search
CPC . A61B 17/17; A61B 17/1703; A61B 17/1739; A61B 17/1764
See application file for complete search history.

(56) References Cited

U.S. PATENT DOCUMENTS

| 2003/0093079 A1 | 5/2003 | Masini |
| 2009/0087276 A1 | 4/2009 | Rose |

(Continued)

FOREIGN PATENT DOCUMENTS

| EP | 2 042 111 A2 | 1/2009 |
| WO | WO 95/17126 | 6/1995 |
| WO | WO 2006/135728 | 12/2006 |

OTHER PUBLICATIONS

International Search Report dated May 11, 2012, International Application No. PCT/EP2012/052814, filed Feb. 17, 2012.

*Primary Examiner* — Anu Ramana

(57) ABSTRACT

A patient specific trial repositioning block is disclosed which extends the know operating technique using patient-specific cutting blocks by virtue of the fact that the soft-tissue situation or ligament tension conditions can be checked and corrected intraoperatively. The trial repositioning block can be dimensioned according to the tibia structure and femur structure. During use of the trial positioning block in an operation, the block can bring the femur to lie in a planned corrected end position on the tibia. Trial repositioning can be performed after the sectioning of the tibia, and the operator, after sectioning of the tibia, can already have an accurate picture of the end result of the operation.

15 Claims, 11 Drawing Sheets

(56) References Cited

U.S. PATENT DOCUMENTS

2009/0088763 A1* 4/2009 Aram ................ A61B 17/155
                                                    606/88
2009/0222014 A1* 9/2009 Bojarski ............ A61B 17/155
                                                    606/88

* cited by examiner

PRIOR ART

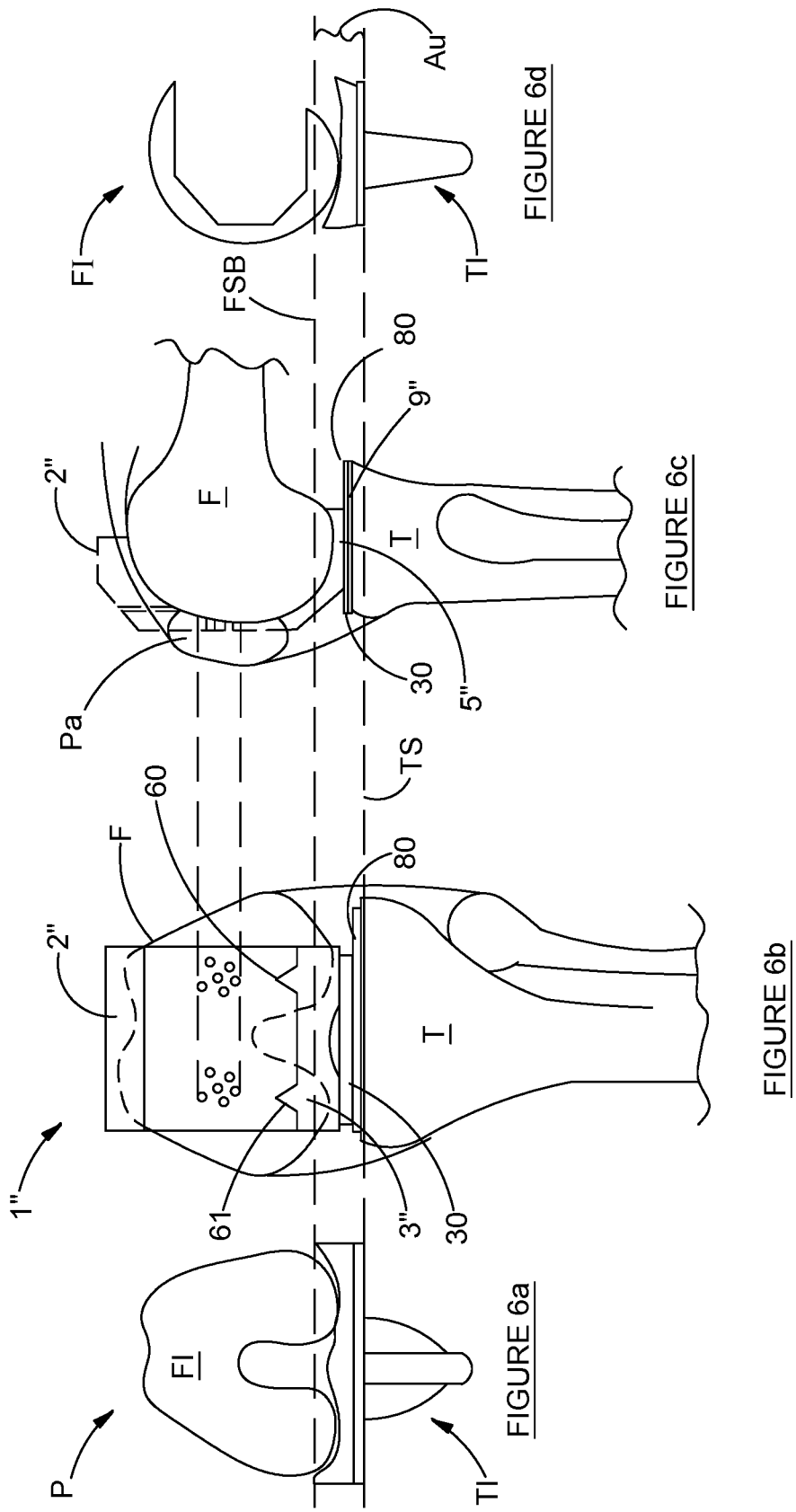

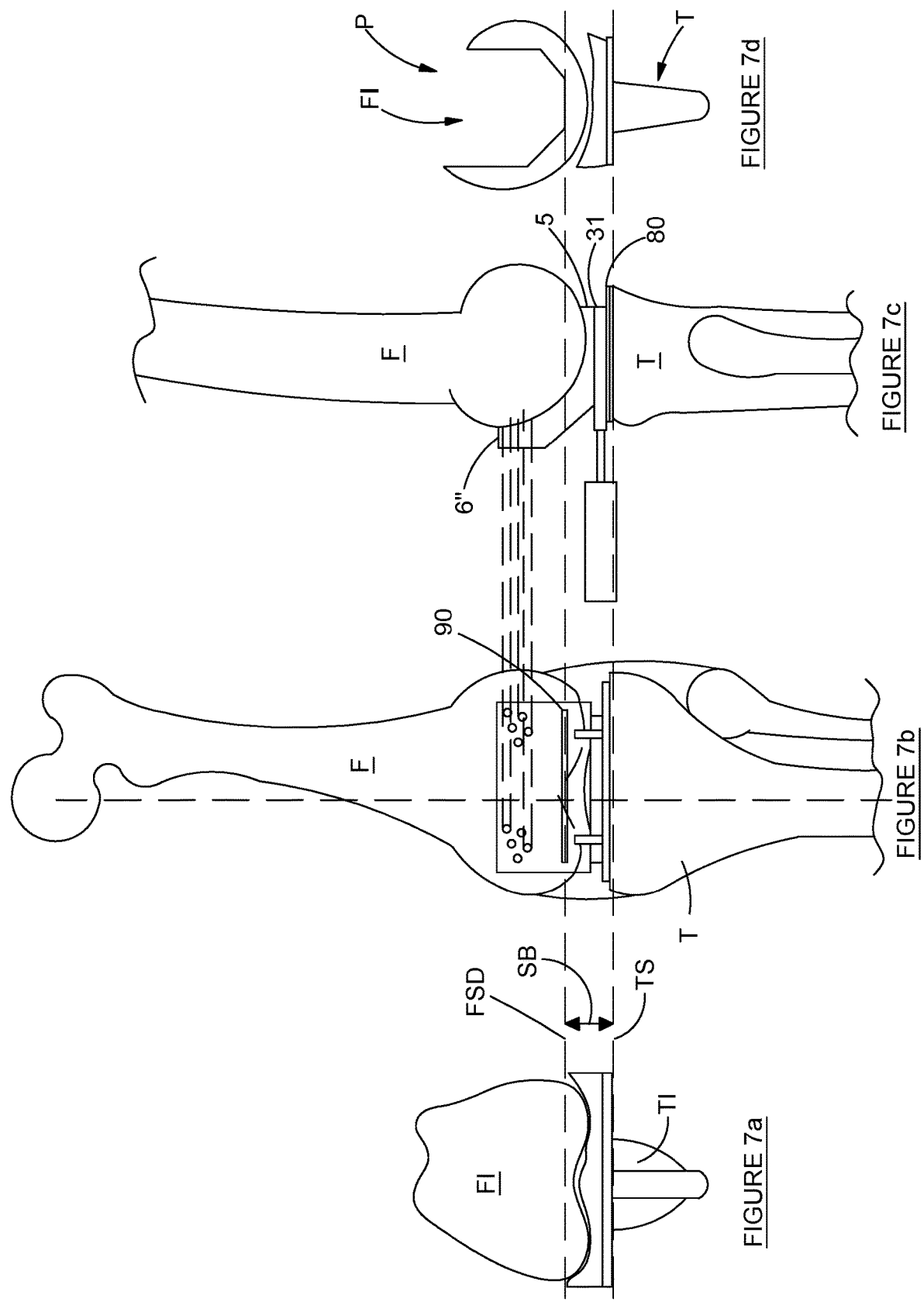

PATIENT-SPECIFIC TRIAL REPOSITIONING BLOCK

This application is the U.S. National Phase under 35 U.S.C. § 371 of International Application No. PCT/EP2012/052814, filed Feb. 17, 2012, which claims priority to Swiss Application No. 00301/11, filed Feb. 21, 2011.

TECHNICAL FIELD

The present invention relates to the field of endoprosthetics, in particular total knee arthroplasty. It relates to a trial repositioning block according to claim 1 as well as a surgical method according to claim 14 comprising the removal and replacement of diseased parts of the knee joint, in particular of the distal end of a femur with a femur implant and a production method according to claim 15.

PRIOR ART

Today's instruments and operation techniques for the implant of a knee endoprosthesis are all developed according to the same principle, i.e., the prosthesis is positioned as anatomically as possible based on bony landmarks.

This takes place through the positioning of cutting blocks or saw guides by different instruments that take the ligament conditions in the knee into consideration or not.

The different bone cuts are guided and precisely resected with an oscillating saw by means of these cutting blocks. There are fundamentally two philosophies thereby in knee arthroplasty: i) "femur first," that is, bone-referenced, or ii) "tibia first," that is, soft tissue-referenced. It is already described in EP 0322363 A1 that achievement of the correct mechanical axis of the leg is one of the most important prerequisites for long life of the knee prosthesis without loosening and pain. In this connection, it is not only a matter of bringing about the correct static knee structure (alignment), but it is likewise important for balanced tension of the knee ligaments to be present, insofar as they still exist, or the correct soft-tissue tension (F. C. Ewald: Biomechanical Indications for Implant Selection III: Knee: Role of Ligaments and Alignment, American Academy of Orthopaedic Surgeons, 54$^{th}$ Annual Meeting, San Francisco, Jan. 22-27, 1987. Instructional Course Number 323).

The primary total knee prostheses usual today are composed of a component fixed to the femur and a component fixed to the tibia, which unlike the hinge prosthesis are not connected to one another by artificial mechanical aids. As in the natural knee joint, the flexible connection between the two components is produced by ligaments and muscles, insofar as they are preserved during the knee arthroplasty, i.e., with the resection and subsequent implant of the prosthesis.

Before the prosthesis components can be attached to the femur and to the tibia by means of clamping, wedging and/or bone cement, the femur and tibia must be shaped to fit the prosthesis with the aid of bone saws and other instruments. The instruments generally offered by the manufacturers of knee prostheses used for this purpose are primarily used to carry out the required corresponding bone cuts on the femur and on the tibia, the so-called osteotomies, with the necessary precision.

It is an essential requirement in this connection that the components of the knee prosthesis that slide against one another when the knee is bent and straightened always have the anatomically correct position relative to one another, i.e. that the mechanical axis of the leg must not deviate from the physiological axis of the leg by more than 3° varus or 3° valgus and that an equilibration of the ligamentous apparatus is achieved which produces good stability of the knee joint during extension as well as during flexion. The object is in each case to obtain a well balanced artificial joint (flexing/extension gap ratio and varus/valgus balance in flexing and extension) which in the HKA (hip-knee-ankle) axis, that is, the mechanical axis of the leg is correctly aligned. Likewise, a full extension as well as the highest possible flexing of the artificial knee joint is to be rendered possible.

The known operation methods try to achieve this as follows:

Femur first (bone-referenced):

Firstly processing of the femur is completed based on bone landmarks. Subsequently, the tibia is resectioned and processing is completed. The actual ligament conditions are not evident to the operator/surgeon until the trial repositioning with the trial prostheses.

With this operation technique it is possible, but not usual, to measure the joint gap measurements with flexing and extension. However, only after the distal cut on the femur. The femur rotation is referenced with most systems based on the dorsal femur condyles and should be parallel to the epicondylar axis or the so-called "Whiteside line."

ii) Tibia first (soft tissue-referenced):

The tibia is first resected and subsequently the cutting blocks are positioned on the femur based on bony landmarks, but taking into consideration the ligament conditions (femur rotation). That means that the ultimate positioning of the femur prosthesis does not always correspond to the bony landmarks, e.g., epicondylar axis, but it can be achieved that it is implanted in a completely balanced manner.

The cutting blocks with both operating techniques are positioned via extramedullary intramedullary alignment instruments, which are aligned based on bony landmarks. With computer navigated operating techniques (CAS), the cutting blocks are also aligned based on the same bony landmarks. The advantage is that the landmarks, axes of the leg, etc. and the cutting blocks are visualized on the screen. The cutting blocks, provided with sensors that are detected by a camera, can now be positioned without additional instruments.

Conclusion: With all techniques the bony landmarks must be defined intraoperatively, which is made difficult in part by soft tissue etc, and requires from the surgeon a high degree of concentration, ability and experience, since the duration of the operation is to be kept as short as possible.

Patient-Specific Cutting Blocks

For some time now various manufacturers have been offering patient-specific cutting blocks. Before the operation a computed tomography (CT) image or magnetic resonance image (MRI) is made of the knee to be treated in order to produce a precise three-dimensional (3D) image and to record the axes of the leg. The 3D data are sent to the prosthesis manufacturer, who can plan the prosthesis and the corresponding cutting blocks based on the exact 3D model of the damaged joint. The physician can process the completed planning on-line and subsequently give his approval to the production of the cutting blocks. Likewise, he can stipulate standard parameters, such as, for example axis data, tibia slope, femur rotation, etc.

Subsequently, he receives the cutting blocks or pin blocks (without saw guide, only for positioning the pins) including the 3D models of the proximal regions of the tibia and of the distal end of the femur. The fact is that although with the patient-specific cutting blocks, thanks to the 3D model, the prosthesis or the bone cuts can be planned and carried out much more exactly, this is in principle just like the non-specific techniques described above, based on the bony landmarks The ligament conditions cannot be taken into consideration during planning. The ligament conditions can be taken into consideration intraoperatively only as described above under "femur first."

In principle, with the known techniques a femur implant is attached to the distal end of the femur or it replaces it and a tibial implant, which has a base plate for attachment to the tibia and an articular surface, replaces the proximal end of the tibia. With a patellar rear-surface replacement, the femur-patella joint can also be supplied. For the attachment of the femur implant, the surgeon resects the distal end of the femur such that it is cut to length to fit precisely complementary to the inner surface of the femoral implant, in order to accommodate it in a positive manner. In the "femur first" operation method, the surgeon subsequently resects the proximal end of the opposite tibia with the so-called tibia cut in order to create the surface to accommodate the complementary base plate. The femoral implant and the tibia base plate are attached, for example; with adhesive means or fasteners to the respective bones. The articular surface is attached to the side of the tibia base plate facing towards the femoral implant. After the patella and the surrounding soft tissue including the ligaments, tendons and muscles have been arranged correctly around the knee again, the femoral implant is able to angle on the joint surface in a manner that comes close to a natural knee movement.

Patient-specific cutting blocks are known, for example, from WO 2010/099142.

With the patient-specific cutting blocks described above, it has not hitherto been possible to monitor the ligament conditions in extension and/or flexing or the HKA axis before the distal femur cut. Only a subsequent correction is possible and entails unnecessary bone loss and an extended operation time.

DESCRIPTION OF THE INVENTION

It is therefore an object of the invention to provide a patient-specific device which makes it possible with the simplest means to take into consideration the soft tissue and ligament conditions intraoperatively, to reduce the duration of the operation and at the same time to increase the quality thereof and thus ultimately to increase the lifetime of the knee arthroplasty.

Furthermore, it is an object of the invention to disclose a method for carrying out a knee arthroplasty, which at least does not have major disadvantages of the known methods.

It is furthermore an object of the invention to disclose a method for producing a patient-specific trial repositioning block, which at least does not have major disadvantages of the described methods.

These and other objects are attained by the features of the trial repositioning block according to claim 1 and the repositioning method according to claim 14.

The solution or invention with the patient-specific trial repositioning block described below enhance the known operation technique with patient-specific cutting blocks in that the soft tissue situation or ligament tension conditions can be reviewed and corrected intraoperatively. It renders possible a surgical procedure in a precision and exactness that has hitherto been available only in the bone-referenced operation technique thanks to a patient-specific cutting block. The present invention corresponds to both applied philosophies: "tibia first" and "femur first."

DETAILED DESCRIPTION

The patient-specific cutting blocks provide substantial cost advantages. They save up to 30 mins in time (1 OP minute=approx. CHF 80, 5 fewer screens sterilized=CHF 100 per screen), which saves the additional cost of a CT scan several times over. The reduced operating time, however, does not only have a positive effect on the cost of the operation, but also reduces considerably the risk of infection for the patient, since the knee has to remain opened for a much shorter time. Further advantages of the new trial repositioning block according to the invention lie in that fewer instruments have to be used during the operation, an that the training requirements for physicians and operating theater staff is reduced.

The CT scans or MRIs produced in advance render possible with this operation method a highly precise implant according to intact anatomical landmarks even with a knee damaged by arthrosis. The patient-specific cutting blocks therefore offer the undisputedly most precise positioning of the knee endoprosthesis, better than CAS and all the other known techniques previously customary with this operation.

The patient risk is furthermore reduced by the following advantages, and the success of the operation is increased:
   Opening of the intramedullary canal is not necessary and thus among other things a considerably reduced risk of a fat embolism
   Reduced operation time since fewer cuts and procedure not so major) and thus a lower risk of infection
   The most precise planning and positioning including the most exact size determination of the implant components
   Possibility of monitoring the mechanical axes of tibia and femur conventionally (e.g., with an alignment rod)

The following disadvantages of the known bone-referenced operating techniques are avoided with patient-specific cutting blocks:
   No possibility of monitoring the ligament conditions in extension and/or flexing before the distal femur cut. Only a subsequent correction is possible, which leads to a longer operation time and unnecessary bone loss.
   Femur rotation corrections are possible via conventional instruments only after the distal cut, which in turn prolongs the operation time.
   The operator does not see the actual ligament tension conditions in extension until after the tibial cut and the distal femur cut. Only after the positioning of the anterior/posterior cutting block on the distal cut can the ligament tension conditions be tested in flexion.

The patient-specific trial repositioning block according to the present invention actually combines according to preferred embodiments the functionality of a trial reposition block, correction block, and cutting block. It thereby provides correction options even before the first femur cut. It ensures that the safest, most exact, quickest and most cost-effective implant method for a knee endoprosthesis is available for the operator.

By means of the new patient-specific femur trial repositioning block, correction block and cutting block, which for the sake of simplicity is referred to below merely as trial repositioning block, a trial reposition can already be carried out after the tibia cut. Thus the operator can already have a very precise idea of the end result after the tibia cut. This has not been possible up until now.

This is now rendered possible by the fact that the outer measurements of the patient-specific trial repositioning block according to the invention are precisely defined. That means that the tibia and the femur structure are calculated into the block, which is sized such that during use in the operation it brings the femur to bear against the tibia in the planned "corrected" final position.

The planning of a knee endoprosthesis on the 3D model according to a CT scan and according to bony landmarks is undisputedly the most precise method of positioning an implant. Only until now with this precise but bone-referenced method the operator has not had any information at all regarding the ligament conditions before he has processed the femur (distal femur cut).

The rotation correction of the femur likewise could be achieved only after the distal femur cut by eye measurement by rotating the 4 in 1 block.

According to the present invention it is now possible to already check the precise planning on the 3D model after the first resected tibia cut likewise planned on the CT model by means of a preferably patient-specific tibia cutting block.

This gives the operator the option of monitoring and if necessary adjusting the soft tissue and the ligament tension before he processes the femur. If necessary, the operator can carry out a ligament release and capsular release in order to balance the joint. Likewise, he can carry out a flexing gap and extension gap measurement and check the entire axis of the leg. This is possible directly with the aid of the trial repositioning block and, if necessary, with the aid of spacers (gap gauge) or with a conventional knee analyzer or pressure sensors. The latter can be integrated according to preferred embodiments into the trial repositioning block according to the invention or detachably fastened in suitable seating regions of the trial repositioning block according to further embodiments.

In the same way different inlay heights (meniscus PE part) and different femur sizes (flexing gap too larger or too small) can be simulated by means of spacers, for example. If then bony corrections regarding varus/valgus axis of the leg and/or femur rotation are necessary despite the release, these can be made directly with the aid of the new trial repositioning block, since it preferably has a number of pairs of correction pin bore holes, which make it possible to set pins for corrected axes. These pin bore holes are arranged on the trial repositioning block such that they provide precisely defined alternative positions for pins in the event of a necessary displacement of the "joint line" or a varus/valgus correction (for the distal femur cut) or for the rotation or for the anterior/posterior (a/p) shift of the femur components (reference holes for pins for attaching the 4 in 1 cutting block).

According to further preferred embodiments of the present invention, the repositioning block comprises insertable inserts by means of which the planned or preset discrete correction positions of the pin bore holes can be selected. According to further advantageous embodiments, the correction position of the pin bore holes can be adjusted as needed on the correction insert.

A brief overview of the operation technique according to the present invention is provided below:
Open knee joint, remove osteophytes
Resect tibia with preferably patient-specific tibia cutting block according to CT planning. For safety, the tibia can possibly be resected less.
Lay protective plate on tibia cut, place distal part of the block according to the invention on the femur, extend knee, measure extension gap and check HKA axis
Flex knee, place patient-specific trial repositioning block on the femur (dorsal block part) fit the patella and carry out the flexing gap measurement
If everything is correct→distal femur cut, drill reference holes for 4 in 1 cutting block, finish processing of tibia and femur, trial reposition, implant.

Correction Options

Soft Tissue and Ligament Release, Dorsal Release (Femur)

If the soft tissue release is not sufficient, the correction pin bore holes defining correction positions can be used in order thus, for example, to carry out "joint line" shifts and varus/valgus corrections or to place the bores for the pins for a conventional distal cutting block according to the desired correction.

The distal reference holes for the 4 in 1 block can be drilled through the block in various rotation positions and a/p positions. Depending on the knee system, it is also possible to change the femur size (anterior or posterior referenced reference holes).

Description of the Cutting Blocks

The Tibia Cutting Block Remains Unchanged (as Offered by Various Manufactures)

It is an important feature of the present invention that the trial repositioning block is produced for the femur in a patient-specific manner. Patient-specific does not mean only the specific adjustment of a proximal surface of the trial repositioning block to the surface of the distal femur region or at least to important landmarks within this region, but also that the trial repositioning block in addition is sized in a precisely defined manner with respect to the distal and the dorsal femur prosthesis structure and tibia structure.

In particular the location and position of the distal and the dorsal sidewall of the trial repositioning block are preset precisely with respect to the proximal surface of the trial repositioning block or at least with respect to the important landmark reference regions inside this proximal surface.

The trial repositioning block according to the present invention defines with its distal side wall a distal reference surface which in the inserted condition according to the surgical plan with extended knee, that is, in the extension condition, preferably comes to rest exactly on the tibia cut or on the protective plate on the tibia cut. According to further embodiments, the distal sidewall is dimensioned thinner so that the distal reference surface does not come to rest directly on the tibia cut or on the protective plate on the tibia cut, but on an additionally inserted spacer of known thickness.

The block can have convex condyles distally and dorsally, likewise medially and laterally.

With its dorsal sidewall, the trial repositioning block according to the present invention defines a dorsal reference surface which in the inserted condition according to the surgical plan with the flexed knee, that is, in the flexion condition, preferably comes to rest exactly on the tibia cut or on the protective plate on the tibia cut. Here too in turn the wall thickness can be reduced and a spacer of known thickness can be inserted.

With respect to the distal and dorsal surface of the trial repositioning block, the proximal surface of the trial repositioning block is produced in a patient-specific manner. The distal and the dorsal reference surface of the associated sidewalls define, measured from the respective cuts, the distal or the dorsal femur structure of the femur components as well as the entire tibia structure.

The thickness of a protective plate for the protection of the tibia cut can be taken into consideration and deducted when sizing the trial repositioning block.

The distal reference surface is arranged such that it sets the joint position in the extended condition.

For the person skilled in the art, it is understandable based on the present teaching that the reference surfaces do not have to be formed by the entire sidewall, but that the actual extension of the flat reference surface can be restricted to a smaller region in the intersection point of the respective reference axis. In extreme cases the entire surface can also have one radius. However, it is preferred to work with a discrete flat reference surface.

The distal and the dorsal reference surface of the trial repositioning block define a common reference angle. According to preferred embodiments, this reference angle corresponds to the flexion angle that is formed by the anatomical femoral axis and the anatomical tibial axis in the flexed condition with the flexing gap measurement (0°/90°).

A trial repositioning block for defining at least one cutting plane on a femur with a total knee arthroplasty according to the present invention comprises at least one patient-specific proximal reference region, which is placed against the distal surface of the femur, and a distal sidewall that defines a distal reference surface, which according to the patient-specific surgical plan with the extension of the knee joint coincides with the tibia cut, and a dorsal sidewall that defines a dorsal reference surface, which according to the patient-specific surgical plan with the flexion of the knee joint coincides with the tibia cut.

According to a preferred embodiment of the trial repositioning block, the distal and/or the dorsal reference surface is respectively formed directly by the surface of the respective distal and/or dorsal sidewall.

According to a further advantageous embodiment, the distal and/or the dorsal reference surface are formed by spacers, which are arranged on the respective sidewalk wherein the spacers preferably can be detachably fastened to the sidewalk.

The trial repositioning block according to the invention is advantageously characterized in that the anterior block part comprises a cutting guide for a distal femur cut, which can guide a tool to produce the distal femur cut, wherein the cutting guide defines a reference plane for the distal femur cut, which is aligned to the distal reference plane of the trial repositioning block such that these two planes correspond to the extension gap according to the patient-specific surgical plan.

The measurement of the extension gap is thus simulated directly by the thickness of the distal sidewall or—according to further embodiments—in addition in a targeted manner a smaller thickness is selected and the measurement is adjusted using a spacer (i.e., a gap gauge). Just like the extension gap measurement, the flexing gap measurement can also be carried out with spacers.

The use of spacers has the additional advantage that various inlay thicknesses can be simulated very easily by means of different spacer thicknesses. Likewise the ratio or the difference between the flexing gap and the extension gap can be measured.

The trial repositioning block according to the invention preferably comprises an anterior and a dorsal block part, which can be detachably fastened to one another in a precisely defined position to one another. The two-part structure with the removable dorsal block part has proven to be particularly advantageous with the extension gap and axis of the leg measurement (HKA axis), since the dorsal part of the block would influence this measurement by deflecting the dorsal capsule and with the flexing gap measurement since the distal part of the block would prevent the measurement with fitted patella.

The dorsal block part preferably surrounds the dorsal condyles of the femur for the flexing gap measurement with fitted patella. The corresponding surface of the dorsal block part in turn is produced in a patient-specific manner based on the 3D data, which are acquired anyway in the CT or MRI for determining the size in the surgical plan.

The trial repositioning block must bear against the joint surface (trochlea) in a precisely fitting manner (necessary so that the osteophytes can be removed in advance and the ligament tensions are not influenced by "deflecting") and surround the outermost points of the distal and dorsal condyles.

The distal and dorsal surface is preferably embodied in a smooth manner.

With the trial repositioning block according to the present invention, the dorsal block part on the dorsal sidewall and the distal block part on the distal sidewall are preferably provided with cutouts to accommodate sensors and/or are directly provided with sensors. The sensors are preferably pressure sensors and particularly preferably arranged medially and laterally on the respective sidewall. The sensors are either already directly integrated from the factory or cutouts or seats are present so that corresponding sensors can be mounted in the clinic upon request or as needed.

With defined smaller measurement: distally and dorsally the surfaces are provided with medial and lateral convex curvatures (condyles). These condyles are available detachable in different thicknesses in order to simulate different corrections. (Resection amount, varus/valgus, femur rotation, inlay thicknesses, femur sizes). Likewise, they can be equipped with sensors. Preferably, the measurement is then carried out with medial or lateral spacers in order to simulate the above-referenced corrections.

According to further advantageous embodiments, in addition to the distal cutting guide the trial repositioning block comprises all further femur cutting guides. The anterior block part thus in addition has a cutting guide for a second (for example, a posterior) femur cut and/or a third (for example, an anterior) femur cut and/or any further femur cuts.

Preferably, an anterior sidewall is provided with positioning means, particularly preferably in the form of different correction pin borehole pairs (+2 mm, +4 mm, 0 nm-2 mm, −4 mm; 1°-3° varus/valgus) in order to be able to distalize, proximalize, varisiate or valgisate a conventional distal cutting block as needed. Of the respectively associated boreholes of a pair, preferably one each is arranged in the medial and one in the lateral region of the sidewall in order to achieve a high precision of the defined plane over the largest possible distance.

In further advantageous embodiments, different boreholes are present (1° in/our 2° in/out 3° in/out 5° in/out 7°/+2 mm, −2 mm) on the distal sidewall based on which the rotation and alp position of the 4 in 1 block (a/p cuts or femur component) can be adjusted. Of the respectively associated bore holes of a pair, preferably in turn one each is arranged in the medial region and one in the lateral region of the sidewall.

The block according to the invention can preferably be designed such that it can directly accommodate cutting blocks of conventional instruments, such as is known for example from WO 2010/099142.

The trial repositioning block according to the invention comprises according to further advantageous embodiments seats for extramedullary axis monitoring instruments, such as are known from the prior art and available on the market.

According to further embodiments according to the invention, in the block according to the invention one or more seats of one/several reference/s for various CAS systems are provided.

The trial repositioning block according to the present invention is preferably produced entirely in a rapid prototyping method. At least the patient-specific portions, in particular the patient-specific proximal reference region and preferably the dorsal and the distal side wall of the dorsal and anterior block parts are produced in a rapid prototyping method. Rapid prototyping methods are understood to be production methods in which components are directly structured based on 3D data, preferably in layers from formless or form-neutral materials. Currently in particular 3D printing methods are possible in which plastics, lime powder with epoxide shell or photopolymers on acyl basis are used or electron-beam melting processes for metals or fused deposition modeling (FDM) methods for acrylonitrile butadiene styrene copolymerisates (ABS) or polycarbonates or laminated object modeling (LOM) methods for paper, plastics, ceramic or aluminum, or laser engineered net shaping (LENS) methods for metals, or laser application welding for metals or selective laser melting (SLM) for metals, plastics or ceramics or selective laser sintering (SLS) for thermoplastic materials (for example: polycarbonates, polyamide, polyvinyl chloride, metals, ceramics) or stereolithography (STL, or SLA) methods for liquid thermosetting materials or elastomers.

The present invention realizes the following advantages compared to patient-specific cutting blocks already available. It takes into consideration the two operation philosophies "bone referenced" and "soft tissue referenced" in that it combines the advantages of both techniques. It already makes it possible after the tibia cut to assess the end result according to the patient-specific surgical plan and, as needed, to make the necessary corrections. Furthermore, a ligament release and capsular release can be carried out before the femur is processed. The ligamentous conditions are the same as with the trial prosthesis or the definitive prosthesis.

In the cases in which the ligamentous conditions, which now can be monitored at an early stage, are correct in connection with the planned cuts, a huge amount of time can be saved. In the cases in which corrections are necessary, these corrections are based directly on the very exact patient-specific planning, which in turn is based on 3D data of a CT scan or an MRI scan.

Thus, for example, a 2° varus correction for the distal cut on the femur, which corresponds exactly to a deviation of the mechanical femoral axis of 2°, can be carried out directly and exactly by the new trial repositioning block with the aid of the positioning means, for example, in the form of pairs of pin boreholes.

With the new method for producing a patient-specific trial repositioning block according to the invention for defining at least one cutting plane on a femur with a total knee arthroplasty, it is important that based on 3D data of the knee to be treated at least one patient-specific proximal reference region, which is placed against the distal surface of the femur F, is produced and a distal sidewall is produced such that it defines a distal reference surface, which according to the patient-specific surgical plan with the extension of the knee joint coincides with the tibia cut. Preferably, furthermore a dorsal sidewall is produced such that it defines a dorsal reference surface, which according to the patient-specific surgical plan with the flexion of the knee joint coincides with the tibia cut.

The sidewalk do not have to be embodied flat throughout thereby, but comprise at least three bearing points, which lie in the respective reference plane and define it. Preferably two lateral bearing regions are embodied, which define the reference plane.

BRIEF EXPLANATION OF THE FIGURES

The invention is explained in greater detail below based on exemplary embodiments in connection with the drawing.

FIG. 2b a view of the proximal side of the trial repositioning block according to FIG. 2a.

FIG. 3a shows in a diagrammatic view in a perspective view from ventro-lateral a knee joint in the flexed condition (flexion) in which after a tibia cut has already been made the trial repositioning block is arranged on the femur to monitor the flexing gap, and FIG. 3b a direct view of the distal side of the trial repositioning block in the flexed knee according to FIG. 3a.

FIG. 5b shows a correction insert for use with a trial repositioning block according to FIG. 5a.

FIG. 5c shows a further correction insert for use with a trial repositioning block according to FIG. 5a.

FIG. 7 shows a diagrammatic overview in which with extended knee in

FIG. 7a a view on the ventral side of a femur implant which is arranged on a tibia implant, in FIG. 7b a view on the distal side of a trial repositioning block arranged on the femur according to a further embodiment with protective plate on the tibia, in FIG. 7c a lateral view of the situation according to FIG. 7b and in FIG. 7d a lateral view of the implants according to FIG. 7a is shown, wherein all views are aligned towards one another with respect to the tibia cutting plane.

WAYS FOR CARRYING OUT THE INVENTION

Figure 1A:
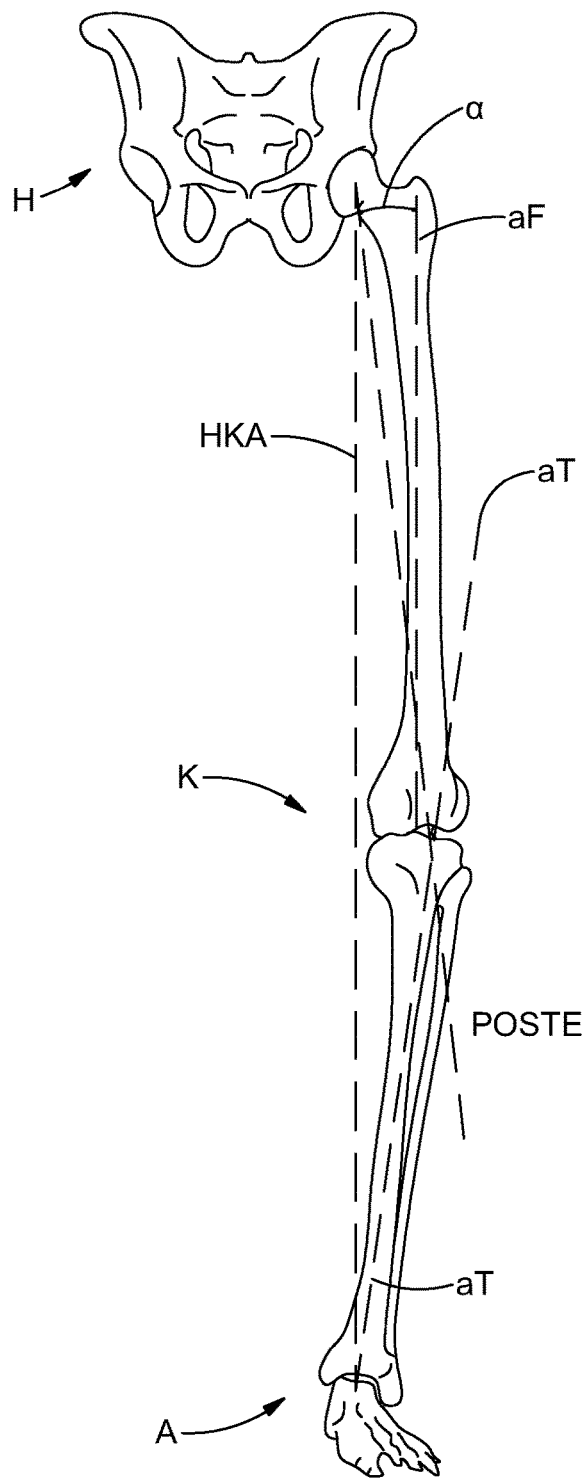
FIG. 1a shows a diagrammatic representation of the mechanical leg skeleton in preoperative condition and FIG. 1b in postoperative condition, wherein in each case a left leg with the relevant axes is shown.
Figure 1B:
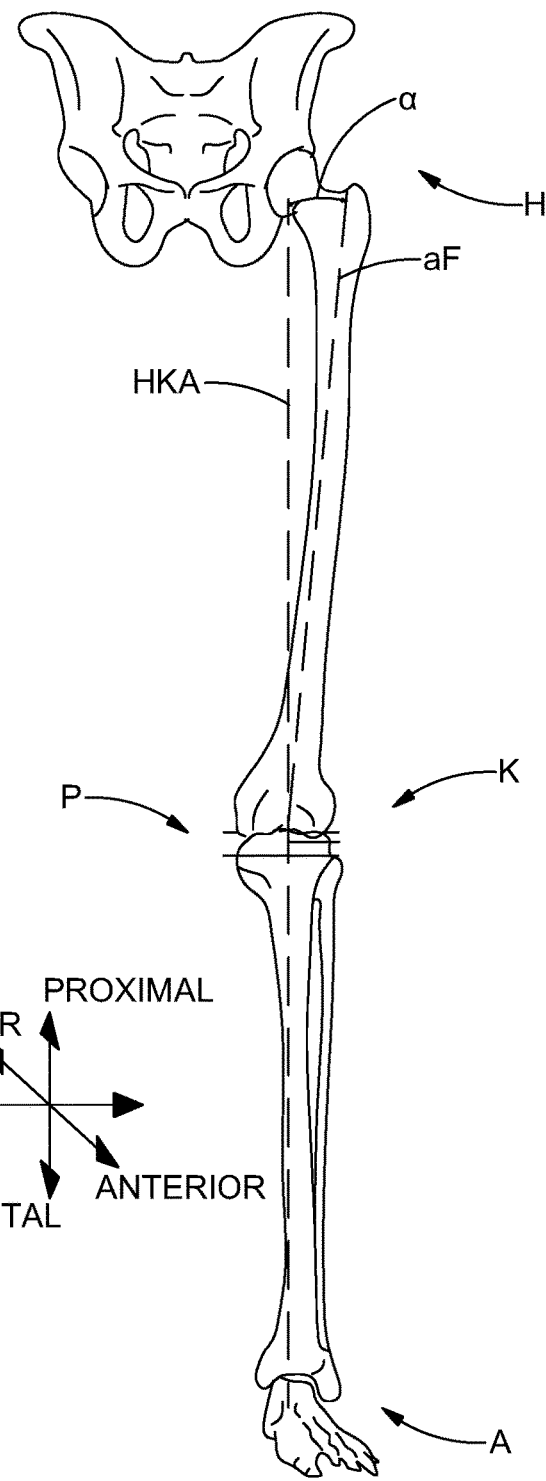

FIGS. 1a and 1b show in a diagrammatic representation the human leg skeleton in the preoperative condition (FIG. 1a) and in the postoperative condition with inserted primary total knee prosthesis (FIG. 1b), wherein respectively a left leg with anatomical axes of tibia aT and femur aF, the HKA axis and the valgus angle α are shown.

Figure 2A:
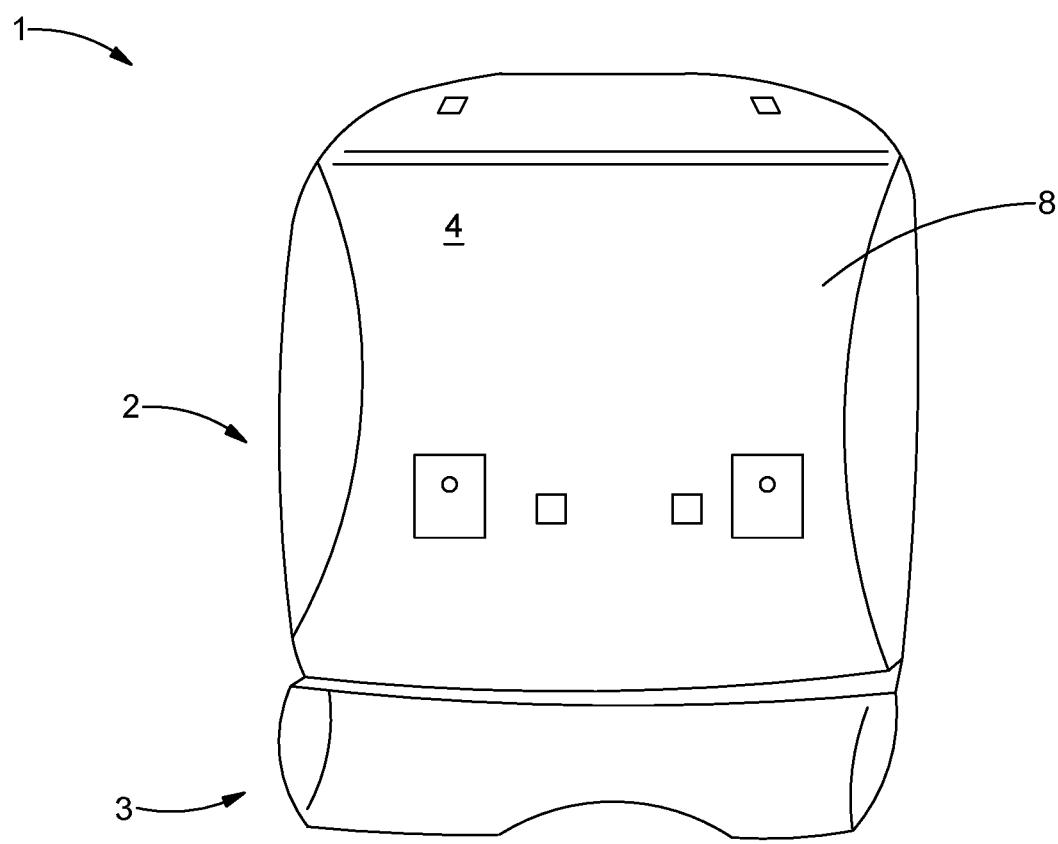
FIG. 2a shows a trial repositioning block according to the invention in the assembled condition in a view of the distal side.

A few important aspects of the present invention are described below based on the different views of a trial repositioning block 1 according to the invention shown in FIG. 2 according to a first embodiment of the present invention. FIG. 2a shows the trial repositioning block 1 in the assembled condition in a view of the distal side. The trial repositioning block 1 is composed of an anterior block part 2 and a dorsal block part 3. The attachment means that hold the two block parts together in a positive and/or non-positive manner in the provided position are not shown in the figure. A distal sidewall 4 defines an essentially flat distal reference surface 8, which according to the patient-specific surgical plan, with the extension of the knee joint coincides with the tibia cut, and with the trial repositioning comes to rest on the cut tibia surface or on a protective plate arranged thereon.

Figure 2B:
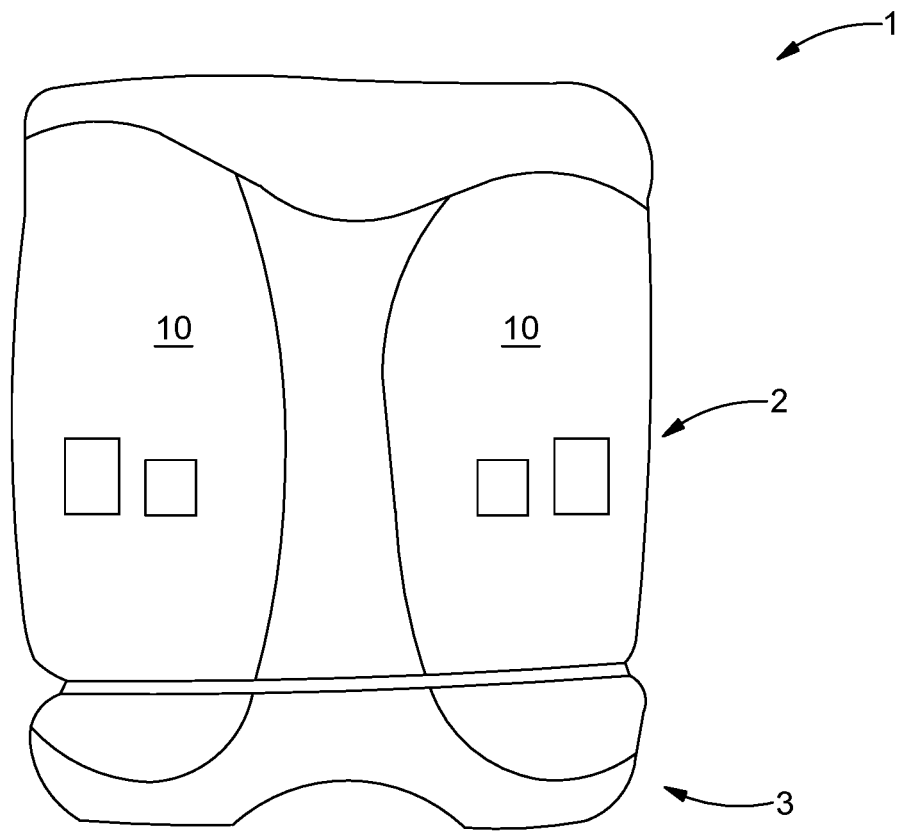
Figure 2C:
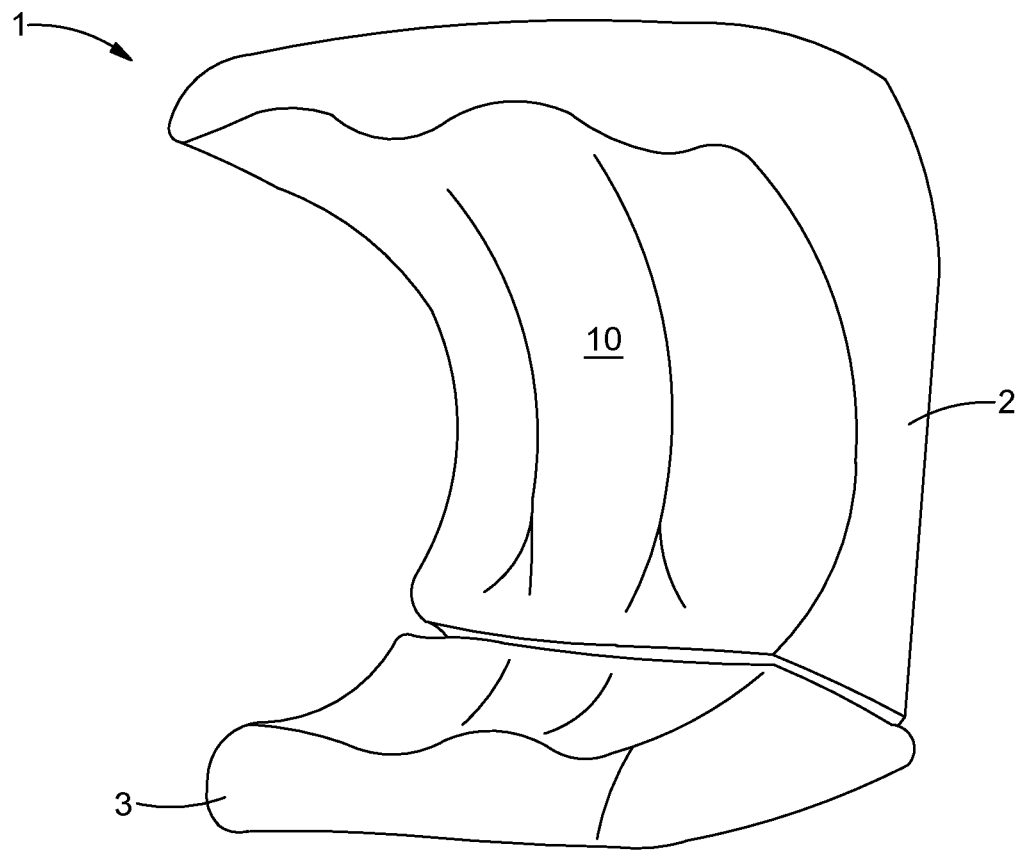
FIG. 2c shows a perspective view obliquely of the proximal side according to FIG. 2b and FIG. 2d the trial repositioning block according to FIGS. 2a-2c, wherein the two sub-units of the trial repositioning block are shown separate from one another in a view according to FIG. 2b

FIG. 2b shows a view of the proximal patient-specifically shaped side of the trial repositioning block 1 according to FIG. 2a.

The perspective view according to FIG. 2c once again clarifies the patient-specific design of the proximal side and the proximal reference region 10 of the trial repositioning block 1. The proximal portions of the anterior block part 2 as well as also of the posterior block part 3 are precisely adjusted to the surface of the patient's femur to be replaced. In the exemplary embodiment shown the patient-specific design of the proximal reference regions is adapted almost over the entire surface to the 3D data of the joint region to be replaced acquired previously, so that an extremely precise positioning of the block 1 on the femur/femur condyles is ensured. The implant shown is also individually adapted to the patient, or to the patient-specific surgical plan with respect to the thickness of the distal sidewall 4 and of the dorsal sidewall 5. Based on the planned joint gap measurements of the surgical plan, the wall thickness 40 of the distal sidewall 4 is selected such in the exemplary embodiment shown that the reference surface 8 (taken together with FIG. 2a) defined by the distal side wall 4 presets the desired extension gap of 18 mm, for example.

Block 1 of FIGS. 2a through 2d does not itself comprise a cutting guide for a distal and any further femur cuts, which can guide a tool for producing these femur cuts. However, it has positioning means in the form of various pin/borehole pairs, by means of which bores to accommodate pins for positioning a conventional cutting block on the femur in can be produced in the exact position. Of the respectively associated bore holes of a pair for the rotation correction one each is arranged in the medial and one in the lateral region of the sidewall 4 in order to achieve a high precision of the defined plane over the largest possible distance.

Figure 2D:
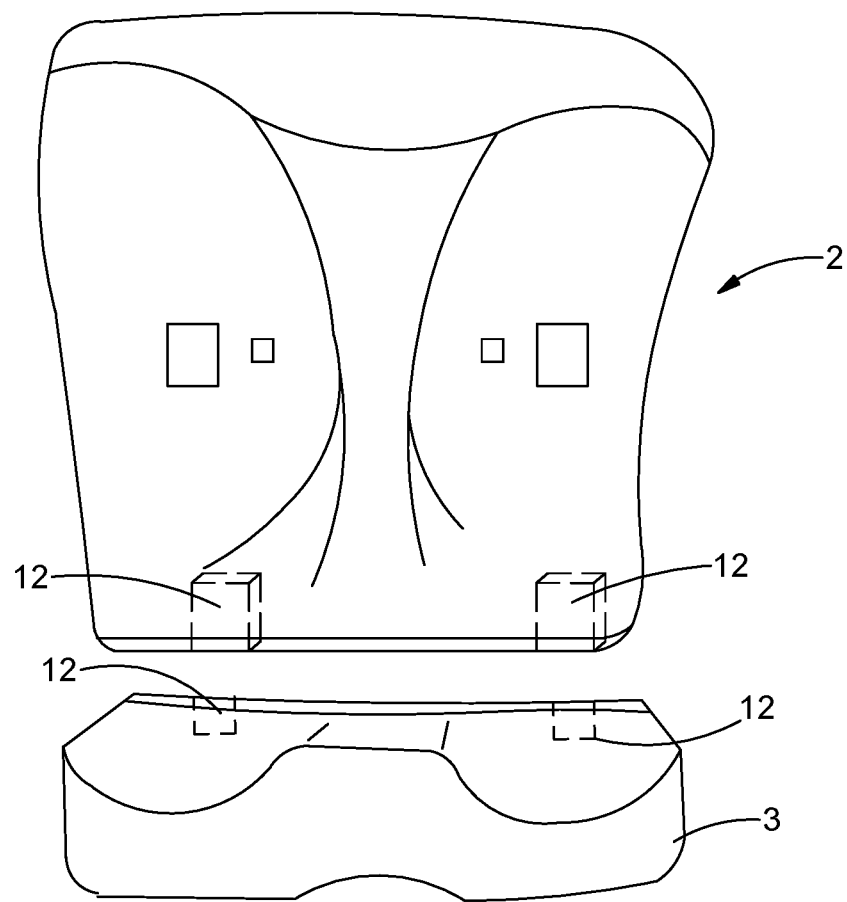

In the distal sidewall 4 of the block 1, as indicated in FIGS. 2a, 2b and 2d, according to preferred embodiments sensors 70 are integrated or can be integrated, which are used for load measurement with extension. The sensors as well as the pin borehole pairs are not shown in all views in FIGS. 2a-2d.

In FIG. 2d the anterior block part 2 and the posterior block part 3 are shown spaced apart from one another. When seen together with FIG. 2c, it is clear that according to preferred embodiments the relative positioning of the two block parts with respect to one another can be produced not only by positive connection means, as is shown below, but also by non-positive means, such as for example magnets 12, which are recessed in the block parts aligned with opposite poles to one another. In FIG. 2d these magnets are indicated by dashed lines.

Figure 3A:
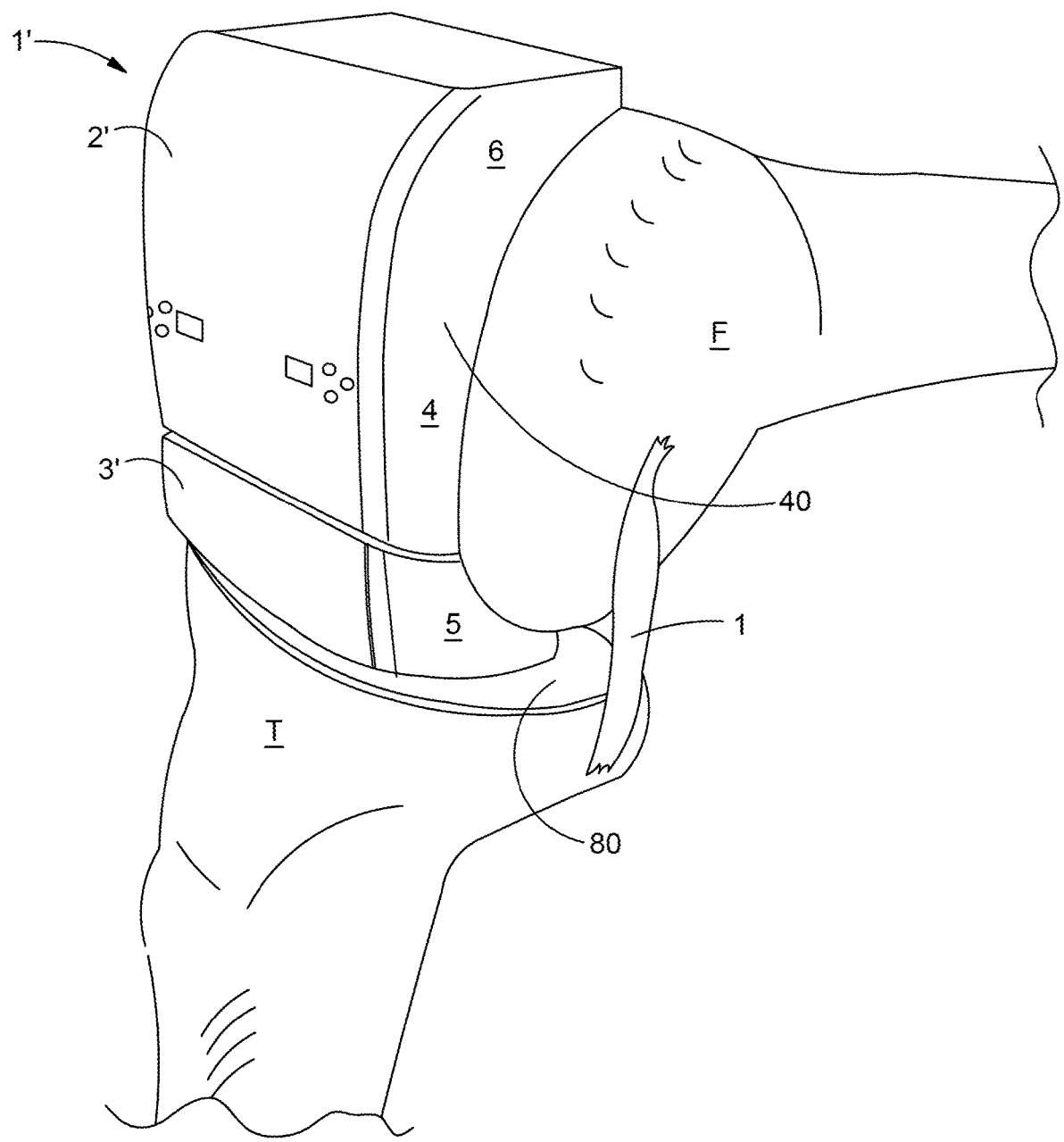

FIG. 3a shows diagrammatically how a two-part trial repositioning block 1' according to one embodiment of the invention which essentially corresponds to the trial repositioning block 1 according to FIG. 2, is arranged in use on a flexed knee. In the figure for better clarity, all soft tissue has been omitted and only one inner ligament I is indicated diagrammatically. A dorsal sidewall 5' of the dorsal block part 3' defines a dorsal reference surface which in the inserted condition according to the surgical plan with flexed knee, that is, in the condition of flexion shown, comes to rest exactly on the tibia cut, or on the protective plate 80 on the tibia cut. The wall thickness of the dorsal side wall 5' is exactly adjusted to the patient-specific surgical plan and defines a dorsal reference surface which, with the flexion of the knee joint, coincides with the tibia cut, and with the trial reposition comes to rest on a protective plate 80 arranged on the tibia cut.

Figure 3B:
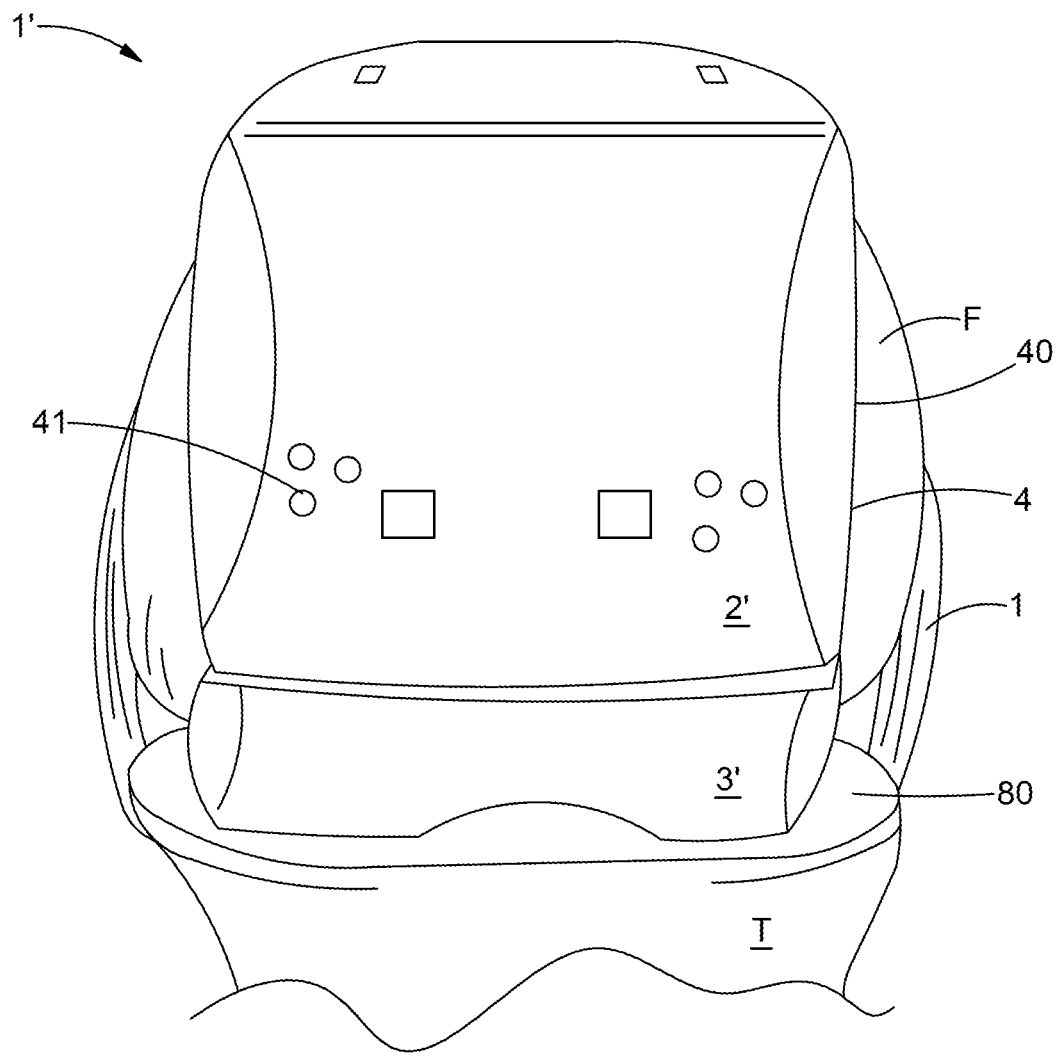

FIG. 3b shows the situation according to FIG. 3a in a view of the distal side surfaces of the two block parts 2' and 3'. The treating surgeon with the aid of the patient-specific trial repositioning block 1 can directly check the flexing gap as it has been produced according to the surgical plan. If he establishes during this check that the dimensioning of the flexing gap and/or the provided rotation does not match the soft tissue situation specific to the patient, he can correct this error immediately with the aid of the correction pin boreholes and make the bores for accommodating the pins in the femur deviating from the surgical plan such that the joint in flexion is optimally balanced in a soft tissue referenced manner.

Figure 4B:
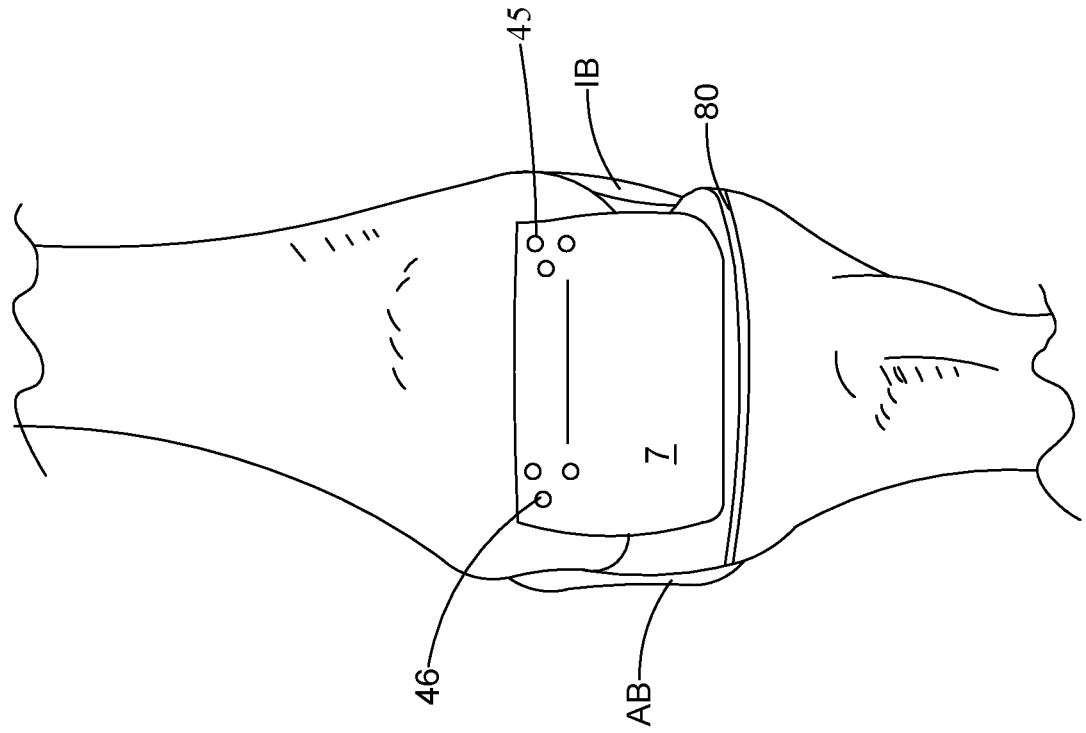
FIG. 4b shows the situation according to FIG. 4a in a view from ventral.
Figure 4A:
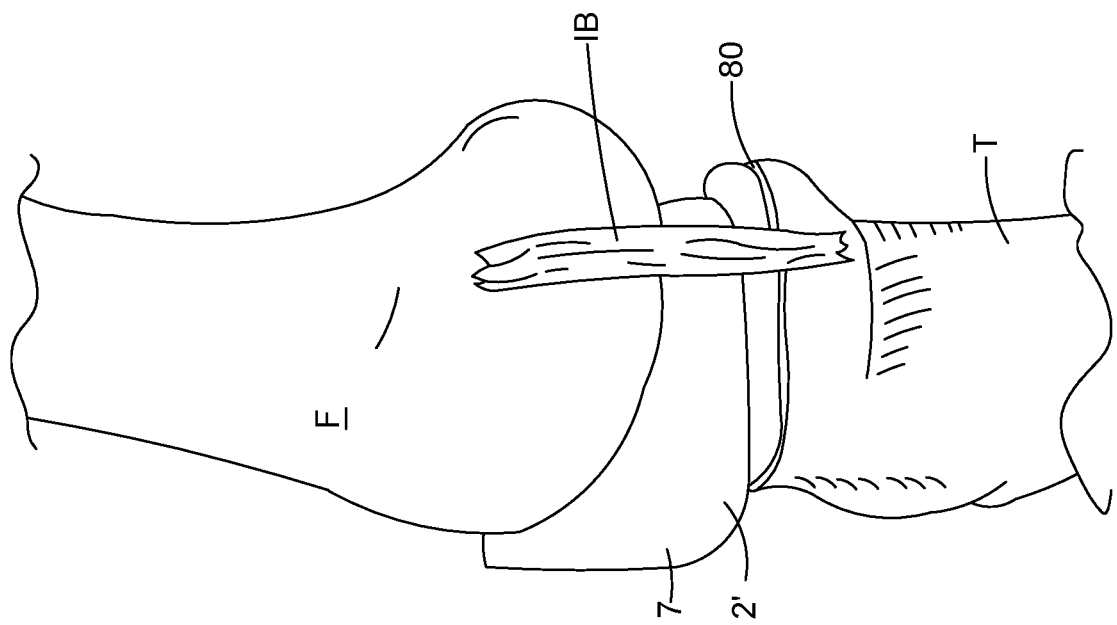
FIG. 4a lateral view of a knee joint in the extended condition (extension) in which after the tibia cut has been made the trial repositioning block is arranged on the femur for monitoring the extension gap, wherein the dorsal part of the trial repositioning block is removed.

In FIGS. 4a and 4b with the knee joint according to FIGS. 3a and 3b with the aid of the anterior block part 2' the trial reposition is carried out with extended knee. It is clear from FIG. 4a that the posterior block part 3' is removed to review the surgical plan in the extension. Only the anterior block part 2' is used in order to carry out any necessary displacement of the "joint line" or a varus/valgus correction (for the distal femur cut). The anterior block part 2' bears with its distal sidewall 4 directly on the protective plate 80 on the tibia cut. In the exemplary embodiment shown, the distal wall surface of the distal side wall 4 thus directly forms the distal reference surface.

If the surgeon establishes that the extension gap according to the surgical plan is not optimally coordinated with the soft tissue situation of the patient, or that the desired varus and valgus angles are not achieved, in turn he can set the bores for the pins by means of the correction pin boreholes 45, 46 arranged in the frontal side wall 7 taking into consideration the necessary corrections.

Figure 5A:
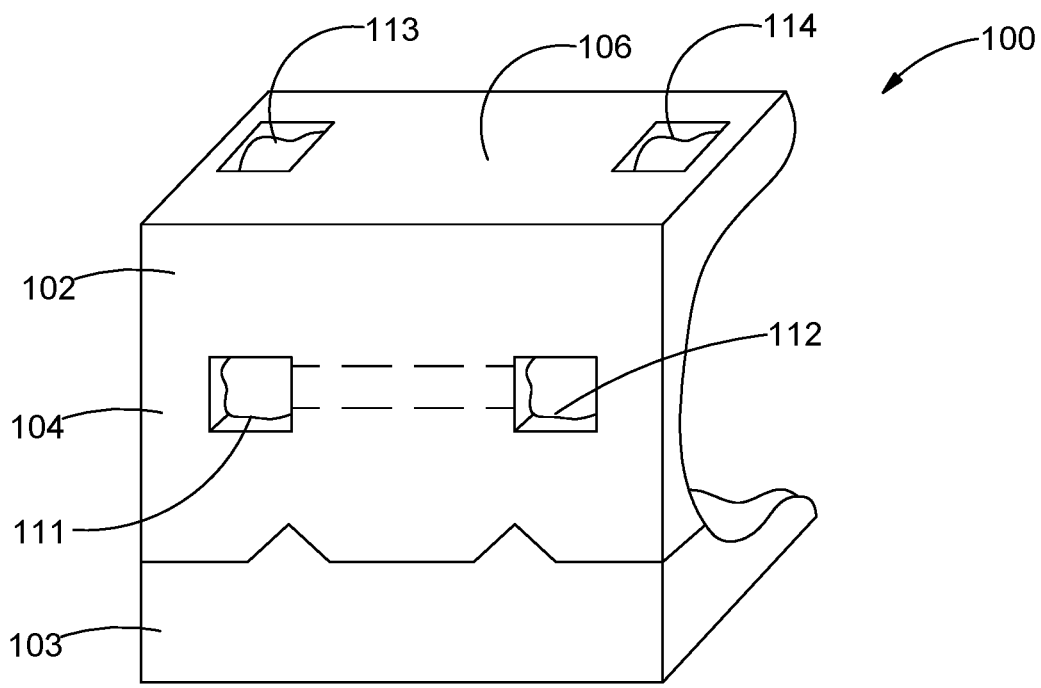
FIG. 5a shows a trial repositioning block according to a further embodiment of the invention for use with correction inserts, which are missing from the figures.

In FIG. 5a a trial repositioning block 100 according to a further embodiment of the present invention is shown. The trial repositioning block 100 in turn is subdivided into an anterior block part 102 and a posterior block part 103. The distal side wall 104 and the ventral side wall 106 of the anterior block part 102 are respectively provided with two seat openings 111, 112, 113 and 114. Different correction inserts 120, 121, as they are shown for example in FIG. 5b and FIG. 5c, can be inserted into the seat openings. The seat openings 111-114 have a defined square cross section and are sized such that the correction inserts 120, 121 can be inserted from the proximal side. The correction inserts comprise respectively two lateral plug-in bodies 122, 123, 124 and 125, which are connected to one another via a support bar 126, 127. The plug-in bodies 122, 123, 124 and 125 the vertical beams 126, 127 are sized such that in the inserted condition from proximal can be pushed into the respective side wall so far that no portions project into the proximal reference region and interfere with the positive closure with the femur surface. Each of the plug-in bodies 122, 123, 124 and 125 has a pin borehole 128.1-128.4.

Figure 5B:
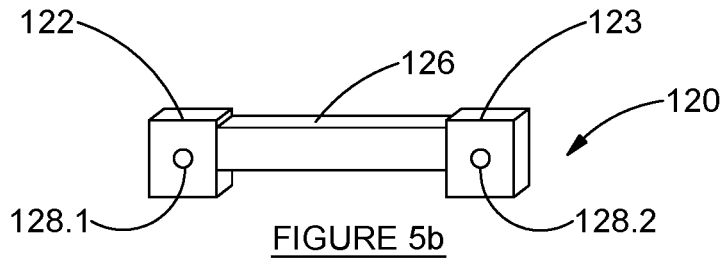

The correction insert 120 shown in FIG. 5b is inserted into the seat openings 113, 114 of the ventral sidewall 106 and in the inserted condition defines with its pair of pin boreholes 128.1 and 128.2 the position provided according to the surgical plan of the two anterior pins, to which subsequently a conventional cutting block can be attached in the planned distal/proximal position with 0 mm and 0° varus/valgus deviation according to surgical plan. If the surgeon establishes during the trial repositioning on the extended knee a correction requirement regarding varus or valgus or with respect to a distal or proximal deviation of the cutting plane of the planned distal femur cut, he can carry out precisely defined corrections by means of a number of preset correction inserts. The correction inserts preferably provide the following correction possibilities and combinations thereof:
Distal/proximal: +1 mm, +2 mm, +3 mm, +4 mm, −1 mm, −2 mm, −3 mm, −4 mm
Varus (respectively left/right): 1°, 2°, 3°, 4°
Valgus (respectively left/right): 1°, 2°, 3°, 4°

The correction insert 121 shown in 5c is inserted into the seat openings 111,111 of the ventral sidewall 104 and in the inserted condition defines with its pair of pin boreholes 128.3 and 128.4 the position provided according to the surgical plan of the two distal pins on which a conventional cutting block can be fixed in the planned position with 0 mm deviation from the anterior/posterior cutting planes and with 0° deviation from the planned inner/outer rotation. If the surgeon establishes during the trial repositioning on the flexed knee a correction requirement with respect to rotation or with respect to an anterior or posterior deviation of the cutting plane of the planned dorsal femur cut, in turn he can carry out precisely defined corrections by means of a number of predetermined correction inserts. The correction inserts preferably provide the following correction possibilities and combinations thereof:
Anterior/posterior: +2 mm, −2 mm
Outer rotation: −1°, −2°, −3°
Inner rotation: 1°, 2°, 3°

Figure 5C:
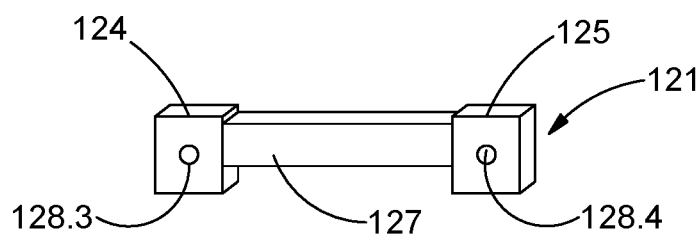

According to further embodiments, not shown in the figures, the correction inserts are embodied such that they are not, like the inserts 120, 121 shown in FIGS. 5b and 5c, inserted from proximal into the corresponding seat openings, but from the respectively other side of the wall. To this end the inserts have on the back positive and/or non-positive connection means so that these correction inserts can be fastened in a detachable manner to the block part. The advantage of this embodiment lies in that the correction inserts can be easily replaced, even when the block part is attached to the femur.

Figure 5D:
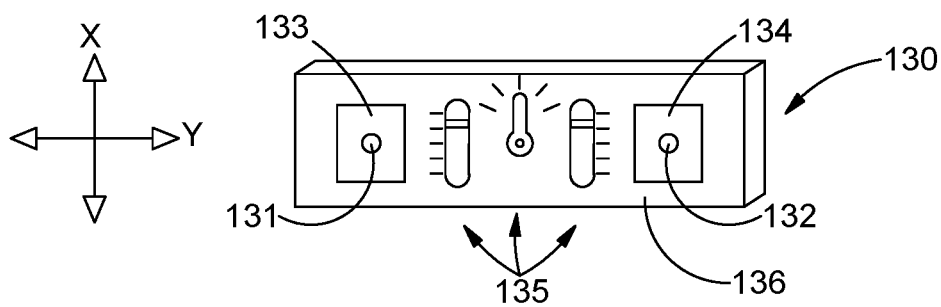
FIG. 5d shows an adjustable correction insert for use with a trial repositioning block according to FIG. 5a FIG. 6 shows a diagrammatic overview in which with the flexed knee is shown FIG. 6a a view on the distal side of a femur implant on a tibia implant, in FIG. 6b a view on the distal side of a trial repositioning block arranged on the femur with protective plate and additional spacer on the tibia in FIG. 6c a lateral view of the situation according to FIG. 6b and in FIG. 6d a lateral view of the implants according to FIG. 6a, wherein all of the views are aligned towards one another with respect to the tibia cutting plane.

FIG. 5b shows a correction insert 130 according to a further preferred embodiment in which the position of the two pin boreholes 131 and 132 in the correction insert can be changed in the x direction and the y direction. The pin boreholes 131 and 132 to this end are arranged respectively on a support plate 133, 134 supported in a displaceable manner inside the correction insert, which by means of the adjustment devices 135 can be brought into a desired x-y position and can be adjusted according to the above-mentioned correction values varus/valgus, distal/proximal, or inner/outer rotation, anterior/posterior. The correction insert 130 shown in FIG. 5d in turn is not, like the inserts 120, 121 shown in FIGS. 2b and 2c, inserted from proximal into the corresponding seat openings, but from the respectively other side of the wall. Its base plate 136 to this end has on the rear wall, which lies at the back in the drawing view, positive and/or non-positive connection means so that the correction insert 130 can be detachably fastened to the block part, 103.

In the overview representations according to FIGS. 6a through 6d, the connection between the sizing of the patient-specific trial repositioning block 1″ according to the invention and the previously compiled surgical plan and the implant to be inserted is clarified once again.

In FIG. 6a a total knee prosthesis comprising a femur implant FI and a tibia implant TI is shown in a view from ventral in the quasi-flexed condition. In FIG. 6d the same total knee prosthesis is shown in a lateral view. The total knee prosthesis to be inserted is selected within the scope of the surgical plan in a fitting manner for the patient. Two planes important for the surgical plan which are preset by the prosthesis are shown by dashed lines in FIG. 6. These are the plane for the tibia cut TS and the plane for the posterior femur cut FSP. In the figure the distance shown between these two planes is 18 mm, for example, which corresponds to the structure height AU of the selected total knee prosthesis.

In general it can be established that according to the present invention this structure height in the flexed condition and the structure height in the extended condition can already be simulated by the patient-specific trial repositioning blocks after the tibia cut has been made, since the respective dorsal or distal sidewall is sized in thickness such that it stipulates the planned structure height with respect to the respective dorsal or distal femur cut, so that the femur already comes to rest in the positions planned in a patient-specific manner during the trial repositioning. These positions can be tested and, if necessary corrected, extremely easily with respect to the correct axial alignments, rotations and angular positions and in particular also with respect to the correct soft tissue tension. This can already be done after the tibia cut has been carried out without any invasion on the femur, that is, without a cut or a bore having been made on the femur.

When reviewing with FIGS. 6b and 6c, it is clear that these two reference planes play the decisive role for sizing the patient-specific trial repositioning block 1″, in particular for the wall thickness of the dorsal sidewall 5″ and the positioning of the pin boreholes and the correction pin boreholes in the distal sidewall 4″.

The trial repositioning block 1″ shown in FIGS. 6b and 6c in turn does not have any integrated cutting guide, but is used by means of pin boreholes to be able to set the pins in a precisely defined manner for a conventional cutting block. With the block 1″, the dorsal reference surface 9″ is not formed directly by the dorsal sidewall 5", but by a spacer 30, which lies between the dorsal sidewall 5" and the protective plate 80. The wall thickness of the dorsal sidewall 5" is reduced by the thickness of the spacer 30 according to the embodiment shown.

It is clear from the view according to FIG. 6c that the separation line between the two block parts according to the present invention is preferably selected such that after the removal of the anterior block part, the patella together with the patellar tendons can be fitted undisturbed. The posterior block part does not touch the patella in the fitted condition.

In the view according to FIG. 6b, positive connection means 60, 61 are shown, which are used for the correct positioning of the anterior block part 2" and the posterior block part 3" with respect to one another. The positive connection means are embodied in the region of the split plane of the two block parts as two laterally upright ribs 60, 61 on the posterior block part 3", which engage in two corresponding grooves 60, 61 in the anterior block part 2".

In FIG. 7 in analogy to FIG. 6 the connection between the sizing of the patient-specific trial repositioning block 1" according to the invention, in particular the distal sidewall thereof and the surgical plan prepared in advance and the implant to be inserted is clarified once again.

In FIG. 7a in turn the total knee prosthesis P comprising the femur implant FI and the tibia implant TI is shown in a view from ventral now in the quasi extended condition. In FIG. 7d the same total knee prosthesis P is shown in a lateral view. In FIG. 7 in turn the tibia cutting planes TS important to the surgical plan are drawn by dashed lines. In the extension a further plane preset by the prosthesis P is highly relevant, namely the plane for the distal femur cut FSD. In a review together with FIGS. 7b and 7c, it is clear that these two reference planes play the decisive role for the sizing of the patient-specific trial repositioning block 1", in particular for the wall thickness of the distal side wall 4" and the positioning of the pin boreholes and the correction pin boreholes in the ventral sidewall 6".

In the exemplary embodiment shown, the distal reference surface 8" is not formed directly by the distal sidewall of the anterior block part 2" but by a distal side wall of a spacer in the form of a knee analyzer 31, as is known from the prior art. With the production of the trial repositioning block according to the invention according to FIG. 7, the wall thickness of the distal sidewall is reduced by the thickness of the knee analyzer 31.

It is clear from FIGS. 7a through 7d that the sum of the wall thickness of the distal sidewall of the anterior block part 2", the thickness of the spacer 31 and of the protective plate 80 corresponds precisely to the width of the extension gap SB between the tibia cut TS and the distal femur cut FSD, as is provided in the surgical plan. In the anterior block part 2" shown, a cutting guide 90 is arranged for guiding a cutting tool or producing the distal femur cut precisely in the plane of the distal femur cut FSD.

LIST OF REFERENCE CHARACTERS

| | |
|---|---|
| A | Ankle |
| AB | Outer ligament |
| aF | Anatomical femoral axis |
| aT | Anatomical tibial axis |
| C | Mechanical axis of the leg |
| D | Mechanical femoral axis |
| E | Resection depth tibia (mm) |
| F | Femur |
| FSD | Distal femur cut |
| FSA | Anterior/ventral femur cut |
| FSB | Dorsal femur cut |
| FI | Femur implant |
| H | Hip |
| IB | Inner ligament |
| K | Knee |
| P | Total knee prosthesis |
| Pa | Patella |
| T | Tibia |
| TI | Tibia implant |
| α | Valgus angle |
| 1 | Trial repositioning block |
| 2 | Anterior block part |
| 3 | Dorsal block part |
| 4 | Distal sidewall |
| 5 | Dorsal sidewall |
| 6 | Ventral sidewall |
| 7 | Frontal/ventral sidewall |
| 8 | Distal reference surface |
| 9 | Dorsal reference surface |
| 10 | Proximal reference region |
| 11 | Reference angle |
| 12 | Magnets |
| 30 | Spacer |
| 31 | Spacer, knee analyzer |
| 40 | Correction pin boreholes |
| 41 | Correction pin boreholes |
| 45 | Correction pin boreholes |
| 46 | Correction pin boreholes |
| 51 | Distal side surface |
| 52 | Anterior sidewall |
| 53 | Anterior side surface |
| 60 | Positive connection means |
| 61 | Positive connection means |
| 70 | Sensor |
| 80 | Protective plate (tibia) |
| 90 | Cutting guide |
| 100 | Trial repositioning block |
| 102 | Anterior block part |
| 103 | Dorsal block part |
| 104 | Distal sidewall |
| 105 | Dorsal sidewall |
| 106 | Ventral sidewall |
| 111-114 | Seat openings |
| 120, 121 | Correction inserts |
| 122-125 | Plug-in bodies |
| 126, 127 | Support bar |
| 128.1-128.4 | Pin boreholes |
| 130 | Correction insert (adjustable) |
| 131, 132 | Pin boreholes |
| 133, 134 | Support plate |
| 135 | Adjustment devices |
| 136 | Base plate |

The invention claimed is:

1. A trial repositioning block for defining at least one cutting plane on a femur of a knee joint of a patient for use in a patient specific surgical plan in a total knee arthroplasty, comprising:
   an anterior block part having a distal sidewall and a patient-specific proximal reference region configured to be placed against a distal surface of said femur, and
   a separate dorsal block part having a dorsal sidewall and a patient-specific proximal reference region configured to be placed against said distal surface of said femur,
   the distal sidewall defining a distal reference surface, which according to said patient-specific surgical plan coincides with a tibia cut when said knee joint is in extension,
   the dorsal sidewall defining a dorsal reference surface, which according to the patient-specific surgical plan coincides with a tibia cut when said knee joint is in flexion, wherein a thickness of the distal sidewall and of the dorsal sidewall is individually adapted to said patient respectively to the patient-specific surgical plan.

2. The trial repositioning block of claim 1, wherein the distal and the dorsal reference surface are formed directly by the surface of the respective distal or dorsal sidewall.

3. The trial repositioning block of claim 1, wherein the distal or the dorsal reference surface are formed by spacers; which are arranged on the respective distal or dorsal sidewalk, the spacers detachably fastened to the sidewalls.

4. The trial repositioning block of claim 1, wherein the anterior block part and the dorsal block part can be selectively connected to one another.

5. The trial repositioning block of claim 4, wherein the anterior block part comprises a positioning means for defining a position for a cutting guide for making a distal femur cut on said femur, wherein the cutting guide or the positioning means define a reference plane for the distal femur cut the reference plane aligned to a distal reference plane defined by the distal sidewall of the trial repositioning block such that these two planes correspond to an extension gap according to the patient-specific surgical plan.

6. The trial repositioning block of claim 5, wherein the anterior sidewall is provided with correction pin borehole pairs or correction inserts configured to distalize, proximalize, varisiate or valgisate a position of the cutting guide for the first distal femur cut as needed.

7. The trial repositioning block of claim 6, characterized in that the correction pin borehole pairs or correction inserts are provided for the following correction positions: +1, +2, +3, +4, 0, −1, −2, −3, −4; 1°, 2°, 3°, 4° varus/valgus in order to be able to distalize, proximalize, varisiate or valgisate a position of a conventional distal cutting block or a cutting guide relative to the trial repositioning block as needed.

8. The trial repositioning block claim 5, wherein the distal block part further comprises pairs of pin holes for use in defining a position of a cutting block or a cutting guide for a dorsal femur cut and anterior femur cut, wherein the pairs of pin holes define the position of the cutting guide, which in turn defines a reference plane for the femur cut, which is aligned to the dorsal reference plane of the trial repositioning block such that these two planes correspond to the flexion gap according to the patient-specific surgical plan.

9. The trial repositioning block of claim 8, wherein the pairs of pin holes are provided for the following correction positions: 0°-7°, inner rotation and outer rotation in 1° steps and +/−1-4 mm anterior/posterior shift.

10. The trial repositioning block of claim 4, wherein the anterior block part comprises a means for defining a position of a cutting guide for an anterior femur cut or a posterior femur cut or further femur cuts.

11. The trial repositioning block of claim 4, wherein the dorsal block part on the dorsal sidewall and the anterior block part on the distal sidewall are provided with cutouts to accommodate sensors and are provided with sensors.

12. The trial repositioning block of claim 4, wherein the anterior block part and the dorsal block part can be detachably connected to one another by means of positive or non-positive connection means and can be positioned in a defined relative position to one another.

13. The trial repositioning block of claim 1, wherein at least the patient-specific proximal reference region and the dorsal and the distal sidewalls of the respective dorsal and anterior block parts are produced in a rapid prototyping method.

14. A method for implanting an implant of a knee endoprosthesis, comprising
carrying out a tibia cut, and
after carrying out the tibia cut, carrying out a trial repositioning using the patient-specific trial positioning block of claim 1.

15. The trial repositioning block of claim 1, wherein the anterior block part comprises a positioning means for defining a position for a cutting block for making at least one distal femur cut on said femur, wherein the positioning means defines a reference plane for the distal femur cut, the reference plane aligned to a distal reference plane defined by the distal sidewall of the trial repositioning block such that these two planes correspond to an extension gap according to the patient-specific surgical plan.

* * * * *